United States Patent
Pullagurla et al.

(10) Patent No.: US 10,723,682 B2
(45) Date of Patent: Jul. 28, 2020

(54) PROCESS FOR THE SYNTHESIS OF DOCOSANOL

(71) Applicant: Biophore India Pharmaceuticals PVT. Ltd., Hyderabad (IN)

(72) Inventors: Manik Reddy Pullagurla, Hyderabad (IN); Jagadeesh Babu Rangisetty, Hyderabad (IN)

(73) Assignee: Biophone India Pharmaceuticals PVT, Ltd., Hyderabad, Telangana (IN)

( * ) Notice: Subject to any disclaimer, the term of this patent is extended or adjusted under 35 U.S.C. 154(b) by 0 days.

(21) Appl. No.: 16/198,862

(22) Filed: Nov. 22, 2018

(65) Prior Publication Data
US 2019/0161425 A1    May 30, 2019

(30) Foreign Application Priority Data
Nov. 24, 2017    (IN) .............................. 201741042223

(51) Int. Cl.
| | | |
|---|---|---|
| C07C 31/125 | (2006.01) | |
| C07C 29/76 | (2006.01) | |
| C07C 29/78 | (2006.01) | |
| C07C 45/29 | (2006.01) | |
| C07C 67/30 | (2006.01) | |
| C07C 29/147 | (2006.01) | |
| C07C 45/38 | (2006.01) | |
| C07C 45/30 | (2006.01) | |

(52) U.S. Cl.
CPC .......... *C07C 31/125* (2013.01); *C07C 29/147* (2013.01); *C07C 29/76* (2013.01); *C07C 29/78* (2013.01); *C07C 45/29* (2013.01); *C07C 45/30* (2013.01); *C07C 45/38* (2013.01); *C07C 67/30* (2013.01); *C07B 2200/13* (2013.01)

(58) Field of Classification Search
CPC ..... C07C 31/125; C07C 29/147; C07C 29/78; C07C 45/29; C07C 29/76; C07C 67/30; C07B 2200/13
See application file for complete search history.

(56) References Cited

FOREIGN PATENT DOCUMENTS

WO    WO-0069484 A1 * 11/2000 ......... A61F 13/8405

OTHER PUBLICATIONS

Katz et al. ("Antiviral activity of 1-docosanol, an inhibitor of lipid-enveloped viruses including herpes simplex", Proc. Natl. Acad. Sci., Dec. 1991, vol. 88, pp. 10825-10829).*

* cited by examiner

*Primary Examiner* — Rosalynd A Keys
(74) *Attorney, Agent, or Firm* — Ling Wu; Stephen Yang; Ling and Yang Intellectual Property (57) ABSTRACT

The present invention relates to a novel process for the preparation of Docosanol (I). More particularly, the invention relates to a novel process for the preparation of Docosanol (I) in a substantially pure form with a purity level of greater than 99.5%. The invention also relates to novel crystalline forms of Docosanol (I) and process for preparation thereof.

(I)

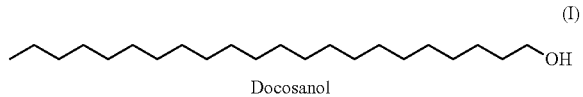

Docosanol

13 Claims, 3 Drawing Sheets

Figure 1: The X-Ray powder diffraction pattern (XRPD) of Docosanol (I) prepared as per Example 4a Figure 2: The X-Ray powder diffraction pattern (XRPD) of Docosanol (I) prepared as per Example 4b Figure 3: The differential scanning calorimetry (DSC) of Docosanol (I) prepared as per Example 4b

PROCESS FOR THE SYNTHESIS OF DOCOSANOL

RELATED PATENT APPLICATION(S)

This application claims the priority and benefit of Indian Patent Application No. 201741042223 filed on Nov. 24, 2017; the disclosures of which are incorporated herein by reference.

FIELD OF THE INVENTION

The invention relates to a novel process for the preparation of Docosanol (I) in a substantially pure form with a purity level of greater than 99.5%. The invention also relates to novel crystalline forms of Docosanol (I) and process for preparation thereof.

BACKGROUND OF THE INVENTION

Docosanol (I) is a drug used for topical treatment for recurrent herpes simplex labialis episodes (cold sores or fever blisters). A saturated 22-carbon aliphatic alcohol, Docosanol (I) exhibits antiviral activity against many lipid enveloped viruses including herpes simplex virus (HSV). It is marketed in the US as 10% topical cream.

The synthesis of Docosanol (I) has been reported in few patents and non-patent literature, the contents of which are hereby incorporated as reference in their entirety.

U.S. Pat. No. 7,718,834 describes the process of preparing primary long-chain alcohols or mixtures thereof by a growth reaction of ethylene on aluminum compounds. Similarly, U.S. Pat. No. 7,141,611 describes a process of obtaining the alcohol mixture by extracting from natural products, using organic solvents with or without saponification.

One of the main disadvantage of the prior art literature reported so far is the use of raw materials from natural sources which provide mixture of fatty acids which are difficult to separate which in turn results in low yield of the desired component. Also, use of highly specific reagents restricts the use of these processes in large scale. Hence, the present inventors have reported a novel synthetic process and purification technique for the preparation of pure Docosanol (I) which is cost effective, simple and employs less expensive chemicals, which makes it more feasible at industrial scale.

The present inventors also found novel crystalline forms of Docosanol (I).

OBJECT OF THE INVENTION

The primary object of the invention is to provide a novel process for the preparation of Docosanol (I).

Another object of the invention is to provide a novel process for the preparation of Docosanol (I) with a purity level of greater than 99.5%.

Another object of the invention is to provide a purification process for obtaining Docosanol (I) in a substantially pure form with a purity level of greater than 99.5%.

Yet another object of the invention is to provide novel crystalline forms of Docosanol (I) and process for preparation thereof.

SUMMARY OF THE INVENTION

Accordingly, there is provided a novel process for the preparation of Docosanol (I) in a substantially pure form with a purity level of greater than 99.5%.

In one aspect of the invention, there is provided a high purity Docosanol (I), wherein the said Docosanol has a purity of greater than 99.5% and one or more of the following;
(i) less than 0.15% n-Tetracosanol as impurity A; and
(ii) less than 0.15% Icosanal as impurity B.

In some embodiment, the high purity Docosanol (I) has a purity greater than 99.5% and total impurities less than 0.5%.

In another aspect of the invention, there is provided a novel process for the preparation of linear long chain aliphatic alcohol Docosanol (I) which comprises of the following steps:
a) oxidation of 1-eicosanol (IV) to form icosanal (III) by treating with a suitable oxidizing agent and base;
b) Wittig reaction between icosanal (III) and a Wittig reagent to form (E)-ethyl docos-2-enoate (II);
c) reduction of (E)-ethyl docos-2-enoate (II) using suitable reducing agent to form Docosanol (I); and
d) optionally, purifying Docosanol (I).

In some embodiment, the oxidizing agent used in step a) of the process for the preparation of Docosanol (I) is selected from sodium hypochlorite, potassium hypochlorite, potassium permanganate, potassium dichromate or the like.

In some other embodiment, the base used in step a) of the process for the preparation of Docosanol (I) is selected from sodium carbonate, potassium carbonate, sodium bicarbonate, potassium bicarbonate, magnesium bicarbonate, calcium bicarbonate or the like.

In yet another embodiment, Wittig reagent used in step b) of the process for the preparation of Docosanol (I) is selected from ethyl-2-(triphenylphosphoranylidene) acetate, methyl (triphenylphosphoranylidene) acetate, triethyl phosphonoacetate, trimethylphosphonoacetate or the like.

In some embodiment, the reducing agent used in step c) of the process for the preparation of Docosanol (I) is selected from sodium borohydride, lithium aluminium hydride, diisobutylaluminium hydride or the like.

In some other embodiment of the invention, 1-eicosanol (IV) is employed as the starting material for the synthesis of Docosanol (I), in place of raw materials from natural sources.

Another aspect of the invention is to provide a process for the preparation of substantially pure Docosanol (I), by purifying from aprotic or protic solvents, which comprises of the following steps:
1) combining Docosanol (I) and aprotic solvent or protic solvent or mixtures thereof;
2) heating the mixture of step 1) to a temperature between 50° C. to 65° C., preferably 50-55° C.
3) cooling the mixture of step 2) between 0° C. to 35° C.; and
4) isolating Docosanol (I) by filtering under vacuum.

In some embodiment, the aprotic solvent used in above described process for the preparation of substantially pure Docosanol is selected from a group comprising of hexane, cyclohexane, toluene, dichloromethane, tetrahydrofuran, ethyl acetate, acetone, 1,4 dioxane, diethyl ether, dimethylformamide, dimethyl sulfoxide or the like or mixtures thereof; and the protic solvent is selected from a group comprising of methanol, ethanol, isopropyl alcohol, isobutyl alcohol, water or the like or mixtures thereof.

In some embodiment, Docosanol (I) produced in the above process after purification is substantially pure and has purity greater than 99.5%.

In another aspect of the invention, there is provided novel crystalline forms of Docosanol (I) and the preparation process thereof.

In some embodiment, there is provided a process for the preparation of crystalline Form A of Docosanol (I) comprising the steps of:
a) providing a solution of Docosanol (I) in ethyl acetate;
b) heating the mixture obtained in step a) between 50° C. to 65° C.;
c) cooling the mixture obtained in step c) between 25° C. to 30° C.; and
d) isolating crystalline Form A of Docosanol (I).

In some embodiment, there is provided a process for the preparation of crystalline Form B of Docosanol (I), comprising the following steps:
a) providing a solution of Docosanol (I) in isopropyl alcohol;
b) heating the mixture obtained in step a) between 50° C. to 65° C.;
c) cooling the mixture obtained in step b) between 25° C. to 30° C.; and
d) isolating crystalline Form B of Docosanol (I).

Figure 1:
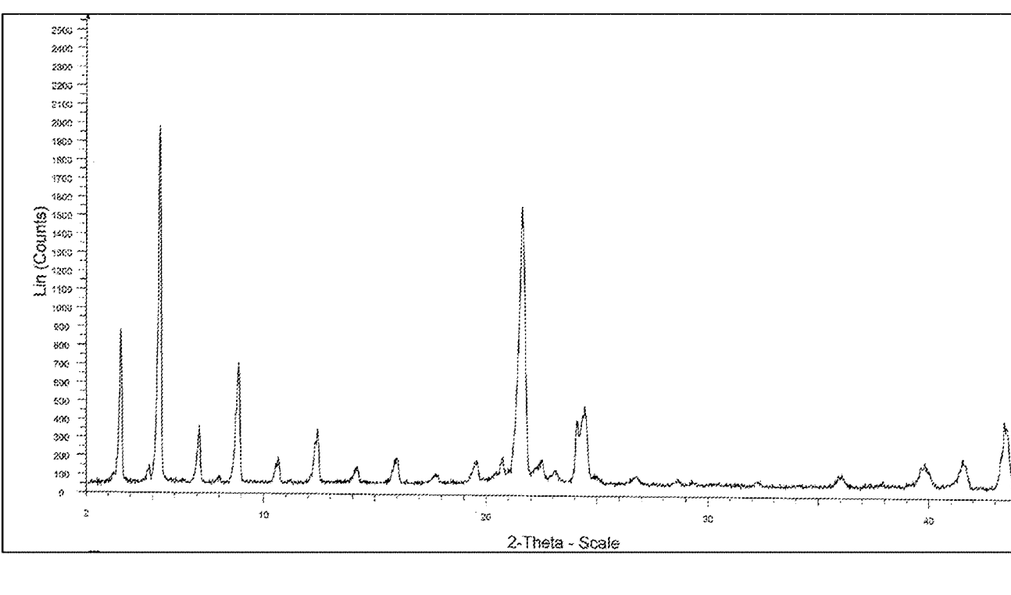

In some embodiment, there is provided a crystalline Form A of Docosanol, characterized by X-ray powder diffraction (XRPD) pattern having peaks expressed as 2θ values at about 3.51, 5.28, 7.05, 8.82 and 21.63±0.2 degrees. In some other embodiment, there is provided a crystalline Form A of Docosanol having X-ray powder diffraction (XRPD) pattern as shown in FIG. 1.

BRIEF DESCRIPTION OF THE DRAWINGS

FIG. 1: Illustrates the X-Ray powder diffraction pattern (XRPD) of Docosanol (I) prepared as per Example 4a

DETAILED DESCRIPTION OF THE INVENTION

The inventors of the present invention have unexpectedly found a novel process for the preparation of Docosanol (I) having purity of greater than 99.5%.

In one aspect of the invention, there is provided a high purity Docosanol (I), wherein the said Docosanol has a purity of greater than 99.5% and one or more of the following;
(i) less than 0.15% n-Tetracosanol as impurity A; and
(ii) less than 0.15% Icosanal as impurity B.

Docosanol (I)

n-Tetracosanol
Impurity A

Icosanal
Impurity B

In some embodiment, the high purity Docosanol (I) has a purity greater than 99.5% and total impurities less than 0.5%.

In another aspect of the invention, there is provided a novel process for the preparation of linear long chain aliphatic alcohol Docosanol (I) which comprises of the following steps:
a) oxidation of 1-eicosanol (IV) to form icosanal (III) by treating with a suitable oxidizing agent and base;
b) Wittig reaction between icosanal (III) and a Wittig reagent to form (E)-ethyl docos-2-enoate (II);
c) reduction of (E)-ethyl docos-2-enoate (II) using suitable reducing agent to form Docosanol (I); and
d) optionally, purifying Docosanol (I).

In some embodiment, the Docosanol (I) according to invention is prepared according to Scheme-1 and the steps are separately described below.

Step a) involves oxidation of 1-eicosanol (IV) with an oxidizing agent in presence of suitable catalyst dissolved in dichloromethane and maintaining the optimum range pH throughout the reaction using suitable base to obtain the product.

In another part of the embodiment the suitable oxidizing agent used in step a) is selected from a group comprising of sodium hypochlorite, potassium hypochlorite, potassium permanganate, potassium dichromate or the like, preferably the oxidizing agent employed is sodium hypochlorite.

Scheme-1

1-eicosanol (IV) → icosanal (III) → (E)-ethyl docos-2-enoate (II) → Docosanol (I) → Purification → Docosanol (I)

In another embodiment, the optimum pH range in step a) has been identified as 8.0-10.0 preferably 8.5-9.5, as any deviation from these conditions may lead to longer reaction time, which may result in formation of impurities. Maintaining the pH in the range of 8.5-9.5 is very crucial and forms one of the novel embodiments of the process.

In some embodiment, the optimum pH range in step a) is maintained by using suitable base selected from a group comprising of sodium carbonate, potassium carbonate, sodium bicarbonate, potassium bicarbonate, magnesium bicarbonate, calcium bicarbonate, or the like, preferably the base employed is sodium bicarbonate.

In some other embodiment, the reaction of step a) is carried in the presence of suitable catalyst such as 2,2,6,6-tetramethylpiperidin-1-yl)oxyl (TEMPO). TEMPO acts as a catalyst and helps in the formation of N-oxoammonium salt which is actually responsible for formation of aldehyde group of Icosanal (III). The Icosanal (III) obtained in step a) is directly used in the step b) without purification. The purity of the crude compound of formula (III) is about 80%. Optionally, it is purified to get purity more than 90%.

Step b) proceeds with Wittig reaction as it involves the reaction between icosanal (III) with suitable Wittig reagent in dichloromethane to obtain (E)-ethyl docos-2-enoate (II) as viscous liquid with more than 90% purity as determined by gas chromatography (GC).

In another embodiment, Wittig reagent used in the second step b) is selected from the group comprising of ethyl-2-(triphenylphosphoranylidene) acetate, methyl(triphenylphosphoranylidene) acetate, triethylphosphonoacetate, trimethylphosphonoacetate or the like, preferably ethyl-2-(triphenylphosphoranylidene)acetate is used.

In some embodiment, the compound of formula (II) obtained in step b) is purified by treating with cyclohexane and cooling to 25-30° C., then filtered to remove undesired solid precipitated from the mixture. The filtrate is treated with methanol and water to remove triphenyl phosphonium oxide (TPP oxide) impurity from the product. The formula (II) is obtained with a purity of greater than about 90%, with TPP oxide impurity content less than about 1.0%. None of the prior art methods discloses process for purification of formula (II), which forms another object of the invention.

Step c) involves reduction of the intermediate ester (II) to crude Docosanol (I). In some embodiment, the viscous liquid ester (II) obtained in the step b) is treated with a suitable reducing agent in a mixture of methanol and tetrahydrofuran solvent and adjusting pH to 1.0-2.0 using hydrochloric acid to obtain crude Docosanol (I). The conversion of conjugated ester of formula (II) to Docosanol (I) by using suitable reducing agent has not been reported in any prior art, which makes another object of the invention.

In another embodiment, suitable reducing agent used in step c), is selected from a group comprising of sodium hydride, potassium hydride, sodium borohydride, lithium aluminium hydride, diisobutylaluminum hydride or the like. Preferably sodium borohydride is used in step c). After completion of reaction, the compound of formula (I) is isolated by using dichloromethane and the obtained solid is washed with ethyl acetate. The Docosanol (I) obtained in step c) is having purity greater than 95%.

Finally, Docosanol (I) obtained in step c) is purified by treating with a suitable aprotic solvent followed by protic solvents, heating to an optimum temperature between 50-65° C., and cooling to temperature between 0-35° C. to isolate the crystalline Docosanol (I) with greater than 99.5% purity. The present invention purification method provides Docosanol with reduced levels of tetracosanol impurity A and other associated process impurities. Optionally, Docosanol (I) produced in any process can be purified by using this purification method. Purification method adopted for Docosanol (I) using aprotic and protic solvents have not been reported in any prior art.

In some embodiment, there is provided a process for the purification of Docosanol (I), comprising:
1) combining Docosanol (I) with aprotic solvent or protic solvent or mixtures thereof;
2) heating the mixture of step 1) between 50° C. to 65° C.;
3) cooling the mixture of step 2) between 0° C. to 35° C.; and
4) isolating Docosanol (I) by filtering under vacuum.

In some embodiment, the aprotic solvent used for the purification is selected from a group comprising of hexane, cyclohexane, toluene, dichloromethane, tetrahydrofuran, ethyl acetate, acetone, 1,4 dioxane, diethyl ether, dimethylformamide, dimethyl sulfoxide or the like or mixtures thereof, preferably ethyl acetate is used in the present invention. The protic solvents used for the purification is selected from a group comprising of methanol, ethanol, isopropyl alcohol, isobutyl alcohol and water or the like or mixtures thereof; preferably isopropyl alcohol is used.

In some embodiment, the purification process of the present invention provides Docosanol (I) having a purity greater than 99.5%.

In some embodiment, the Docosanol (I) obtained after purification is having total impurities less than 0.5% (w/w), more preferably less than 0.2% (w/w), still more preferably less than 0.15% (w/w), each single known impurity more specifically the n-tetracosanol impurity of formula A, the icosanal impurity of formula B, (E)-ethyl docos-2-enoate impurity of formula C and 1-eicosanol impurity of formula D level in the Docosanol (I) are found to be less than 0.15% (w/w); and any unknown impurity less than 0.10% (w/w), which forms another embodiment of the invention.

n-Tetracosanol
Impurity A

Icosanal
Impurity B (E)-Ethyl docos-2-enoate
Impurity C

1-Eicosanol
Impurity D

In another embodiment, Docosanol (I) obtained after purification is reported to have residue on ignition less than 0.10% (w/w); moisture content less than 1% (w/w) and heavy metals content less than 20 ppm.

In yet another embodiment, Docosanol (I) obtained in the present invention is having purity greater than 99.5% and total impurities less than 0.5% and more preferably less than 0.15% (w/w).

In another aspect of the invention, there is provided novel crystalline forms of Docosanol (I) and the preparation process thereof.

Figure 2:
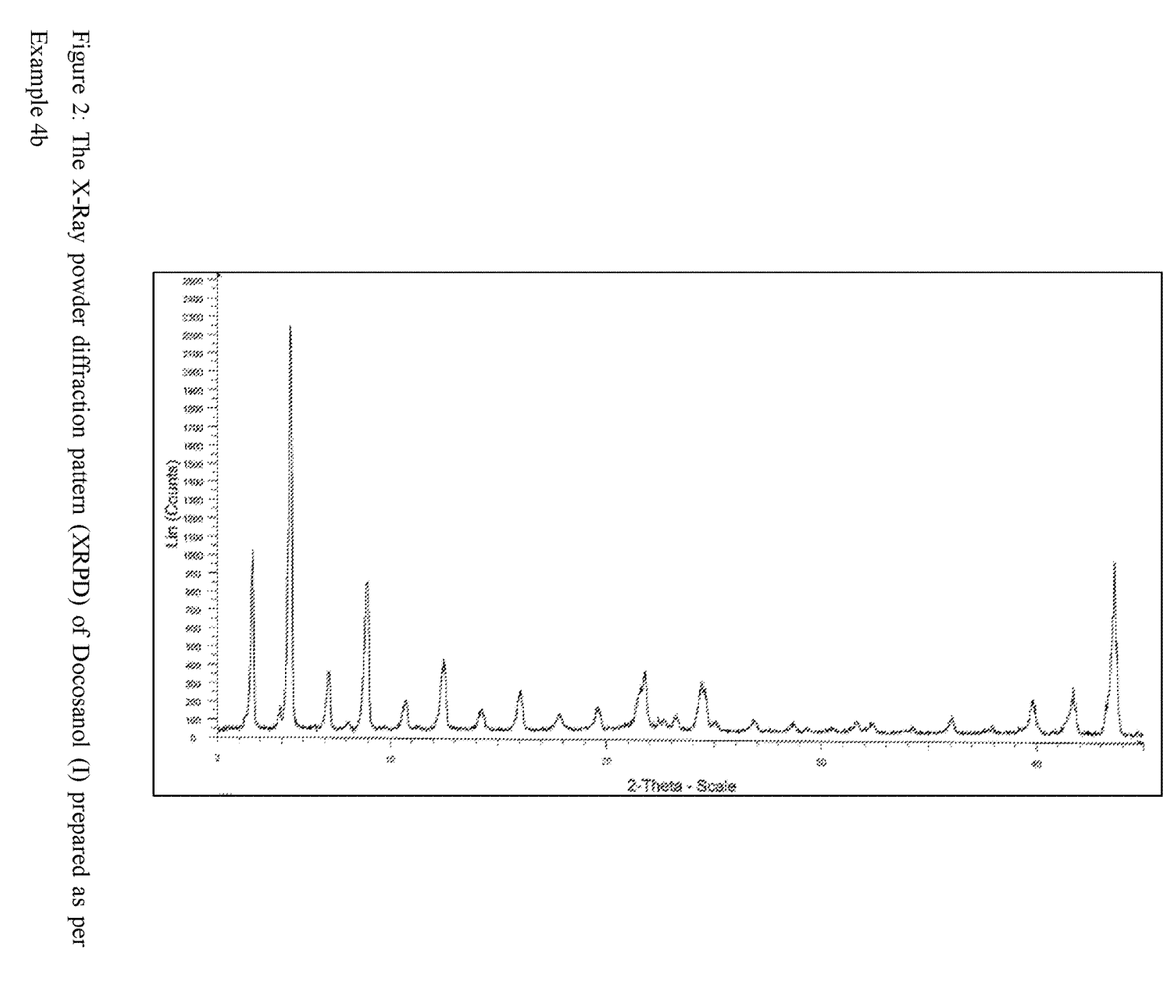
FIG. 2: Illustrates the X-Ray powder diffraction pattern (XRPD) of Docosanol (I) prepared as per Example 4b

The crystalline forms of Docosanol (I) obtained after purification from aprotic or protic solvents were characterized by the X-Ray powder diffraction (XRPD) pattern as shown in FIG. 1 and FIG. 2.

In some embodiment, there is provided a process for the preparation of crystalline Form A of Docosanol (I) comprising the steps of:
a) providing a solution of Docosanol (I) in ethyl acetate;
b) heating the mixture obtained in step a) between 50° C. to 65° C.;
c) cooling the mixture obtained in step c) between 25° C. to 30° C.; and
d) isolating crystalline Form A of Docosanol (I).

A crystalline Form A of Docosanol (I) obtained by stirring the solution of Docosanol in aprotic solvent at a temperature in the range of 50° C. to 65° C. to form a clear solution. The product is isolated by cooling the solution to a temperature range of 0° C. to 35° C. for a period of 60 minutes to 2 hours as described in Example-4a.

The crystalline Form A of Docosanol (I) is prepared as per Example 4a and is characterized by X-Ray powder diffraction (XRPD) pattern as shown in FIG. 1 and the 2 theta values provided in Table 1.

TABLE 1

X-ray diffraction data of Docosanol (I) Form A

| 2(θ) deg. | Relative Intensity (%) |
|---|---|
| 3.51 | 44.2 |
| 4.76 | 6.1 |
| 5.28 | 100 |
| 7.05 | 18.3 |
| 8.82 | 35.3 |
| 10.60 | 9.3 |
| 12.39 | 17.2 |
| 14.17 | 7.0 |
| 15.94 | 9.5 |
| 17.74 | 5.3 |
| 19.54 | 8.8 |
| 20.71 | 10.0 |
| 21.63 | 78.2 |
| 22.48 | 9.4 |
| 23.13 | 6.5 |
| 24.12 | 20.3 |
| 24.44 | 24.1 |
| 36.1 | 6.3 |
| 39.86 | 9.6 |
| 41.63 | 10.4 |
| 43.5 | 21.1 |

In some embodiment, there is provided a crystalline Form A of Docosanol, characterized by X-ray powder diffraction (XRPD) pattern having peaks expressed as 2θ values at about 3.51, 5.28, 7.05, 8.82 and 21.63±0.2 degrees. In some other embodiment, there is provided a crystalline Form A of Docosanol having X-ray powder diffraction (XRPD) pattern as shown in FIG. 1.

In some embodiment, there is provided a process for the preparation of crystalline Form B of Docosanol (I), comprising the following steps:
a) providing a solution of Docosanol (I) in isopropyl alcohol;

b) heating the mixture obtained in step a) between 50° C. to 65° C.;
c) cooling the mixture obtained in step b) between 25° C. to 30° C.; and
d) isolating crystalline Form B of Docosanol (I).

Another crystalline Form B of Docosanol (I) is formed by stirring the solution of Docosanol in protic solvent at a temperature in the range of 50° C. to 65° C. to form a clear solution. The crystalline form of Docosanol (I) is isolated by cooling the solution to a temperature between 0° C. to 35° C. for a period of 60 minutes to 2 hours as described in Example-4b.

The crystalline Form B of Docosanol (I) prepared as per Example-4b is characterized by X-ray powder diffraction (XRPD) pattern as shown in FIG. 2 and the 2 theta values provided in Table 2.

TABLE 2

X-ray diffraction data of Docosanol (I) form B

| 2(θ) deg. | Relative Intensity (%) |
|---|---|
| 4.83 | 7.70 |
| 5.30 | 100 |
| 7.13 | 16.50 |
| 8.05 | 4.20 |
| 8.91 | 37.8 |
| 10.73 | 9.6 |
| 12.46 | 19.4 |
| 14.23 | 7.4 |
| 16.01 | 12.0 |
| 17.82 | 6.50 |
| 19.63 | 8.10 |
| 21.57 | 13.6 |
| 21.77 | 16.9 |
| 23.24 | 6.5 |
| 24.43 | 14.5 |
| 36.07 | 6.5 |
| 39.86 | 10.9 |
| 41.74 | 14.0 |
| 43.67 | 44.4 |

In some embodiment, there is provided a crystalline Form B of Docosanol characterized by X-ray powder diffraction (XRPD) pattern having peaks expressed as 2θ values at about 5.30, 8.91, 12.46, 21.77, 43.67±0.2 degrees. In some other embodiment, there is provided crystalline Form B of Docosanol having X-ray powder diffraction (XRPD) pattern as shown in FIG. 2.

The purity of Docosanol (I) and its related substances or impurities may be analyzed using various methods. A representative useful Gas chromatography (GC) method is described below.

Experimental Conditions:
Column: DB-5, 30 m×0.53 mm ID, 1.5 μm film thickness
Column flow: 2.0 mL/min
Carrier gas: Nitrogen
Injection mode: split
Detector temp: 300° C.
Diluent: chloroform
Run time: 40 min The following examples further illustrate the present invention, but should not be construed in anyway as to limit its scope.

EXAMPLES

Example-1

Preparation of Icosanal (III)

100 g (0.335 moles) of 1-eicosonol (IV) and dichloromethane were added to a round bottom flask at 25-30° C. and temperature was raised to 35-40° C. to get the clear solution. The reaction mass was cooled to 25-30° C. and 0.47 g (0.003 moles) of (2,2,6,6-tetramethylpiperidin-1-yl) oxyl (TEMPO) was added. A mixture of 9-12% aqueous sodium hypochlorite and sodium bicarbonate solution (8%) were then added for 1-2 hours to maintain pH between 8.5 to 9.5. After completion of reaction, 40% aqueous sodium thiosulphate pentahydrate solution was added to the reaction mixture and stirred for 5 minutes at 25-30° C. The reaction mass was then extracted with dichloromethane and distilled off under reduced pressure till 6 volumes of dichloromethane remains. The intermediate Icosanal (III) so obtained can be immediately used in the next step.

Purity %: 80.0

Example-2

Preparation of (E)-ethyl Docos-2-enoate (II)

In a clean and dry round bottom flask, intermediate Icosanal (III) dissolved in dichloromethane as obtained in the Example-1 and 140 g of ethyl 2-(triphenylphosphoranylidene) acetate were added at 25-30° C. and the reaction mixture was heated for 4-5 hours at 45-50° C. After completion of reaction, the dichloromethane solvent was distilled off under vacuum and the crude so formed was washed with cyclohexane. The crude so obtained was cooled to 25-30° C., 400 mL of cyclohexane was added and stirred for 30 minutes. Filtered the reaction mixture under vacuum to remove the precipitated solid and washed with cyclohexane. To the filtrate 140 mL of methanol was added and stirred for 30 minutes at 25-30° C. To this 60 mL water was added and layers were separated. The organic layer was distilled off under vacuum to yield viscous liquid (E)-ethyl docos-2-enoate (II).

Yield %: 77-81; Purity %: 92.0.

Example-3

Preparation of Crude Docosanol (I)

In a clean and dry round bottom flask, 100 g of the (E)-ethyl docos-2-enoate (II) was dissolved in 1000 mL of tetrahydrofuran and 200 mL methanol at 25-30° C., then cooled to 10-15° C. 41 g of sodium borohydride was added portion wise for 1-2 hours. The reaction mass was stirred for 1 hour at 25-30° C. and maintained for 20-24 hours at 60-65° C. After completion of reaction, the reaction mass was cooled to 25-30° C. and slowly the above reaction mass was added to 1000 mL of water at 15-20° C. The pH of the reaction was adjusted to 1.0-2.0 using concentrated hydrochloric acid and temperature was raised to 25-30° C. The organic solvent was removed under reduced pressure below 50° C. till 11-12 volumes of reaction mass remains. The reaction mass was cooled to 30-35° C. and extracted with dichloromethane. The total organic layer was collected and washed with water then the solvent was distilled off under vacuum to obtain crude Docosanol (I).

Yield %: 55-60; Purity %: 99.0

Example-4

Purification of Crude Docosanol (I)

a) In a clean and dry round bottom flask, 100 g (0.306 moles) of crude Docosanol (I) was taken in 400 mL of ethyl acetate at 25-30° C. and heated to 50-55° C. to form a clear solution. The reaction mixture was then cooled for 60-90 minutes at 25-30° C. The solid so obtained was filtered under vacuum, washed with ethyl acetate and dried under vacuum.

Yield %: 55-60; Purity %: 99.7; XRPD: As depicted in FIG. 1.

b) In a clean and dry round bottom flask, 100 g (0.306 moles) of crude Docosanol (I) was taken in 400 mL of isopropyl alcohol at 25-30° C. and heated to 50-55° C. to form a clear solution. The reaction mixture was then cooled for 60-90 minutes at 25-30° C. The solid so obtained was filtered under vacuum, washed with isopropyl alcohol and dried under vacuum.

Figure 3:
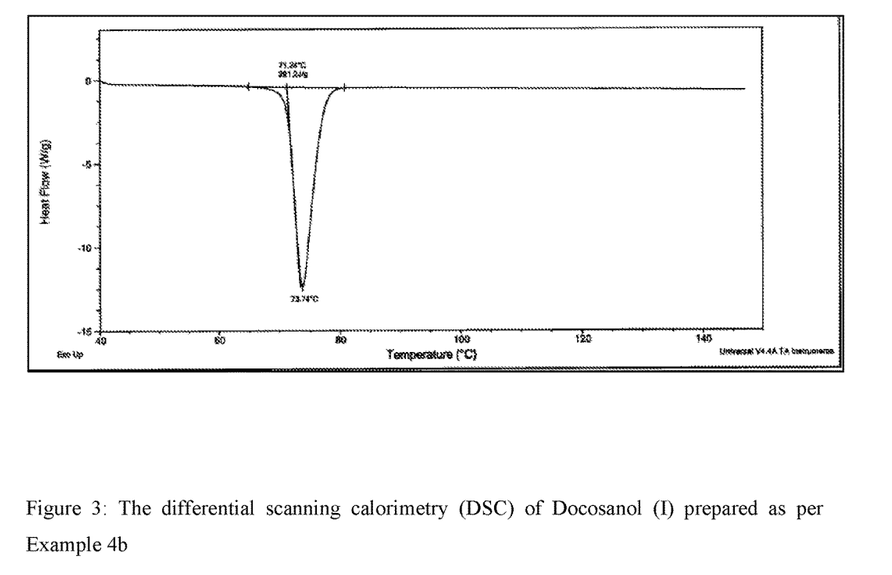
FIG. 3: Illustrates the differential scanning calorimetry (DSC) of Docosanol (I) prepared as per Example 4b

Yield %: 80-85; Purity %: 99.85; XRPD: As shown in FIG. 2; DSC: FIG. 3.

c) In a clean and dry round bottom flask, 100 g of (0.306 moles) of crude Docosanol (I) was taken in 400 mL of ethyl acetate at 25-30° C. and heated to 50-55° C. to form a clear solution. The reaction mixture was then cooled for 60-90 minutes at 25-30° C. The solid so obtained was taken in 400 mL of isopropyl alcohol at 25-30° C. and heated to 50-55° C. to form a clear solution. The reaction mixture was then cooled for 60-90 minutes at 25-30° C. The solid so obtained was filtered under vacuum, washed with isopropyl alcohol and dried under vacuum.

Yield %: 70-80; Purity %: 99.9; XRPD: As depicted in FIG. 2.

The invention claimed is:

1. A substantially pure Docosanol compound of formula (I), wherein the substantially pure Docosanol compound comprises n-Tetracosanol impurity A less than 0.15%, and Icosanal impurity B less than 0.15%

2. A process for the preparation of Docosanol (I), comprising:
    a) oxidation of 1-eicosanol (IV) to form icosanal (III) by treating with a suitable oxidizing agent and base;
    b) Wittig reaction between icosanal (III) and a Wittig reagent to form (E)-ethyl docos-2-enoate (II);
    c) reduction of (E)-ethyl docos-2-enoate (II) using suitable reducing agent to form Docosanol (I); and
    d) optionally, purifying Docosanol (I).

3. The process as claimed in claim 2, wherein the oxidizing agent used in step a) is selected from sodium hypochlorite, potassium hypochlorite, potassium permanganate or potassium dichromate.

4. The process as claimed in claim 2, wherein step a) is carried out in the presence of base selected from sodium carbonate, potassium carbonate, sodium bicarbonate, potassium bicarbonate, magnesium bicarbonate or calcium bicarbonate.

5. The process as claimed in claim 2, wherein the Wittig reagent used in step b) is selected from ethyl-2-(triphenylphosphoranylidene) acetate, methyl(triphenylphosphoranylidene) acetate, triethyl phosphonoacetate or trimethylphosphonoacetate.

6. The process of claim 2, wherein the reducing agent used in step c) is selected from sodium borohydride, lithium aluminium hydride or diisobutylaluminium hydride.

7. A process for the purification of Docosanol (I), comprising:
    1) combining Docosanol (I) with aprotic solvent or protic solvent or mixtures thereof;
    2) heating the mixture of step 1) between 50° C. to 65° C.;
    3) cooling the mixture of step 2) between 0° C. to 35° C.; and
    4) isolating Docosanol (I) by filtering under vacuum.

8. The process as claimed in claim 7, wherein the aprotic solvent is selected from a group comprising of hexane, cyclohexane, toluene, dichloromethane, tetrahydrofuran, ethyl acetate, acetone, 1,4 dioxane, diethyl ether, dimethylformamide, dimethyl sulfoxide or mixtures thereof; and the protic solvent is selected from a group comprising of methanol, ethanol, isopropyl alcohol, isobutyl alcohol, water or from mixtures thereof.

9. The process as claimed in claim 7, wherein Docasanol (I) obtained is crystalline Form A and the process comprises the following steps:
    a) providing a solution of Docosanol (I) in ethyl acetate;
    b) heating the mixture obtained in step a) between 50° C. to 65° C.;

c) cooling the mixture obtained in step b) between 25° C. to 30° C.; and d) isolating crystalline Form A of Docosanol (I).

10. The process as claimed in claim 7, wherein Docasanol (I) obtained is crystalline Form B of Docosanol (I) and the process comprises the following steps:

a) providing a solution of Docosanol (I) in isopropyl alcohol;

b) heating the mixture obtained in step a) between 50° C. to 65° C.;

c) cooling the mixture between 25° C. to 30° C.; and d) isolating crystalline Form B of Docosanol (I).

11. The process as claimed in claim 7, wherein the Docosanol (I) has a purity of greater than 99.5%.

12. A crystalline Form A of Docosanol, characterized by X-ray powder diffraction (XRPD) pattern having peaks expressed as 2θ values at about 3.51, 5.28, 7.05, 8.82 and 21.63+0.2 degrees.

13. The crystalline Form A of Docosanol as claimed in claim 12 having X-ray powder diffraction (XRPD) pattern as shown in FIG. 1.

* * * * *